United States Patent [19]

Schwartz et al.

[11] Patent Number: 5,366,880

[45] Date of Patent: Nov. 22, 1994

[54] ANTIBIOTIC AGENT

[75] Inventors: Robert E. Schwartz, Westfield; Prakash S. Masurekar, Warren; David F. Sesin, Rahway; Jerrold M. Liesch, Princeton Junction; Thomas C. Hallada, Westfield; Otto D. Hensens, Red Bank, all of N.J.

[73] Assignee: Merck & Co., Inc., Rahway, N.J.

[21] Appl. No.: 66,282

[22] Filed: May 21, 1993

Related U.S. Application Data

[62] Division of Ser. No. 640,457, Dec. 19, 1990.

[51] Int. Cl.$^5$ ............... C12P 17/18; C12P 13/00; C12P 7/24; C12P 7/02
[52] U.S. Cl. ............................. 435/119; 435/128; 435/147; 435/155
[58] Field of Search ............... 435/119, 255.1, 128, 435/147, 155; 514/9, 11; 530/317, 323

[56] References Cited

U.S. PATENT DOCUMENTS 4,737,487 4/1988 Watts et al. .................. 514/15
5,021,341 6/1991 Giacobbe et al. ............. 435/71.1

FOREIGN PATENT DOCUMENTS 0359529 3/1990 European Pat. Off.

OTHER PUBLICATIONS

Kurokawa, et al., J. Am. Chem. Soc. 108: 6041–6043 (1986).

Cram, et al., Org. Chem. 2D Ed. McGraw Hill Pub. Co., pp. 607–613 (1964).

Primary Examiner—Douglas W. Robinson
Assistant Examiner—Maria Luisa Osoteo
Attorney, Agent, or Firm—Elliott Korsen; Mark R. Daniel

[57] ABSTRACT

A new antibiotic cyclic lipopeptide having the formula

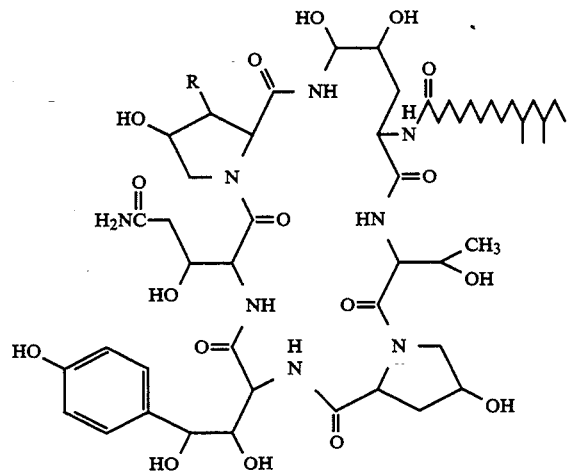

wherein R is H or OH and a method of producing is described. The agent has very high activity against human pathogens and is of very low mammalian toxicity.

1 Claim, 2 Drawing Sheets

FIG. I

ANTIBIOTIC AGENT

This is a division of application Ser. No. 07/640,457, filed Dec. 19, 1990.

The present invention is directed to a compound having the formula (I)

wherein R is H or OH, and to a method of producing same.

When R is H, the compound is hereinafter designated Compound IA. When R is OH the compound is hereinafter designated Compound IB.

The structure of the compounds have been determined by detailed analyses of spectral characteristics.

Compound IA has the following spectral characteristics:

MASS SPECTRAL DATA

Electron impact (EI, 70 eV) and low resolution Fast Atom Bombardment (FAB; MS and MS-MS) mass spectral data were obtained on a Finnigan-MAT TSQ70B mass spectrometer. GC-MS analyses of the TMS (trimethylsilyl) derivatives of total acid hydrolyzates were performed on the same instrument. High resolution FAB measurements were recorded on a Finnigan-MAT MAT90 instrument.

Compound IA has the molecular formula $C_{50}H_{80}N_8O_{17}$ [from M+Cs]+: calcd 1064.5641, found 1064.5585) by FAB-MS. GC-MS analysis of the TMS derivative of the total acid hydrolysate indicated approximately one equivalent each of threonine, 3-hydroxyglutamic acid and 10,12-dimethyltetradecanoic acid plus two equivalents of 4-hydroxyproline.

Figure 1:
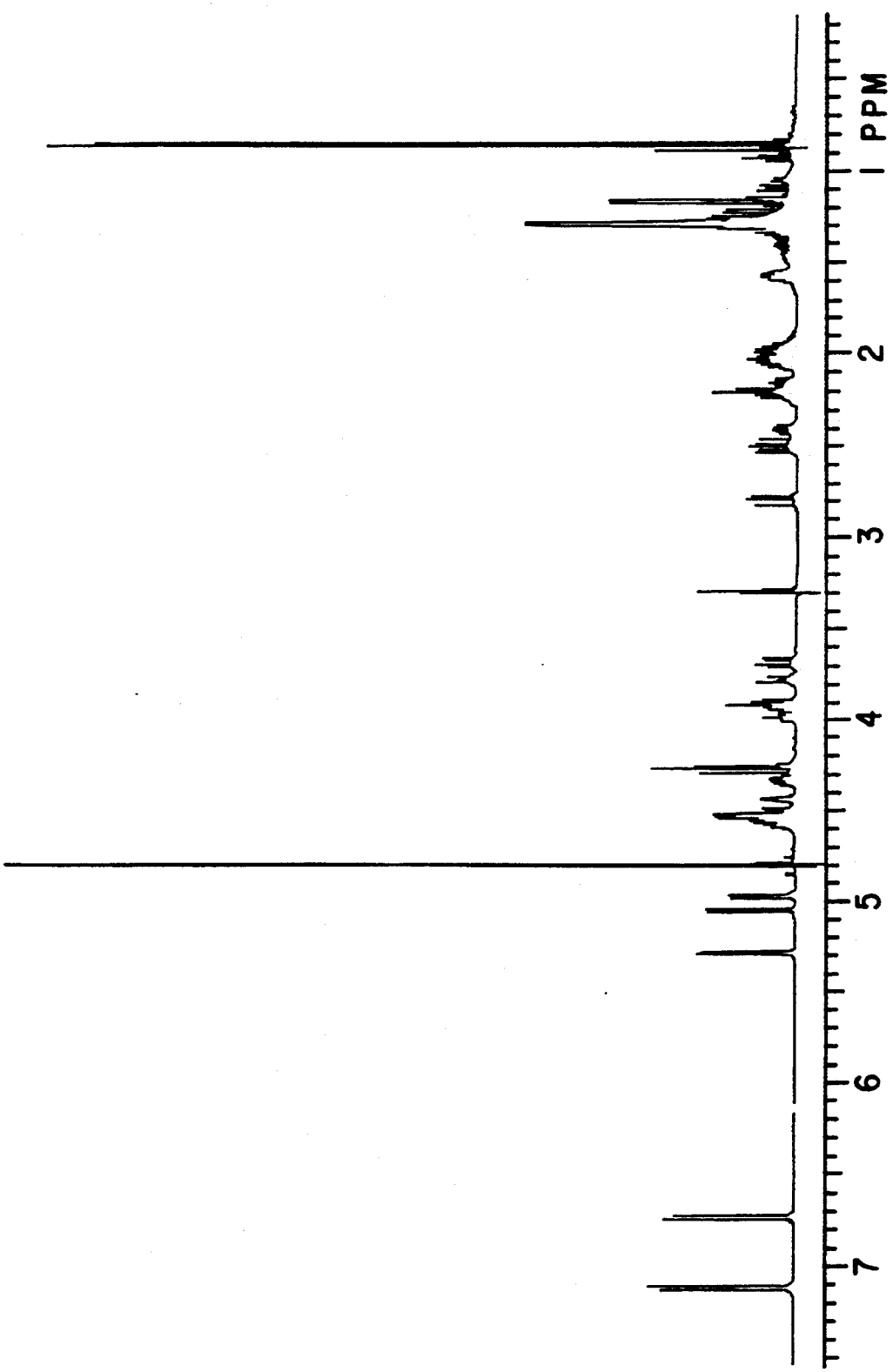

NMR SPECTRAL DATA $^1H$ NMR Spectrum: in $CD_3OD$ at 400 MH$_z$seen in FIG. 1; and $^{13}C$ NMR Chemical Shifts ($CD_3OD$): 11.6, 19.7, 20.2, 20.7, 27.0, 28.1, 30.3 (2x), 30.6, 30.8, 31.2 31.3, 32.9, 34.9, 36.7, 38.1, 38.5 (2x), 39.4, 45.9 51.2, 56.1, 56.3, 57.1, 57.9, 58.3, 60.7, 62.4, 68.2, 70.6, 70.9, 71.0, 71.3, 73.8, 75.8, 76.9, 116.2 (2x), 129.6 (2x), 133.0, 158.5, 169.2, 172.5, 172.9, 173.4, 174.5, 174.6, 175.7, 177.3 ppm.

Compound IB has the following spectral characteristics:

MASS SPECTRAL DATA

Compound IB has the molecular formula $C_{50}H_{80}N_8O_{18}$ (from [M+Cs]+: calcd 1080.5590, found 1080.5344) by FAB-MS. GC-MS analysis of the TMS derivative of the total acid hydrolyzate indicated approximately one equivalent each of threonine, 4-hydroxyproline, 3-hydroxyglutamic acid, 3,4-dihydroxyproline, and 10,12-dimethyltetradecanoic acid. FAB-MS-MS of the [M+H]+ion indicates that IB contains 3,4-dihydroxy-proline at the position preceeding the threonine residue.

Figure 2:
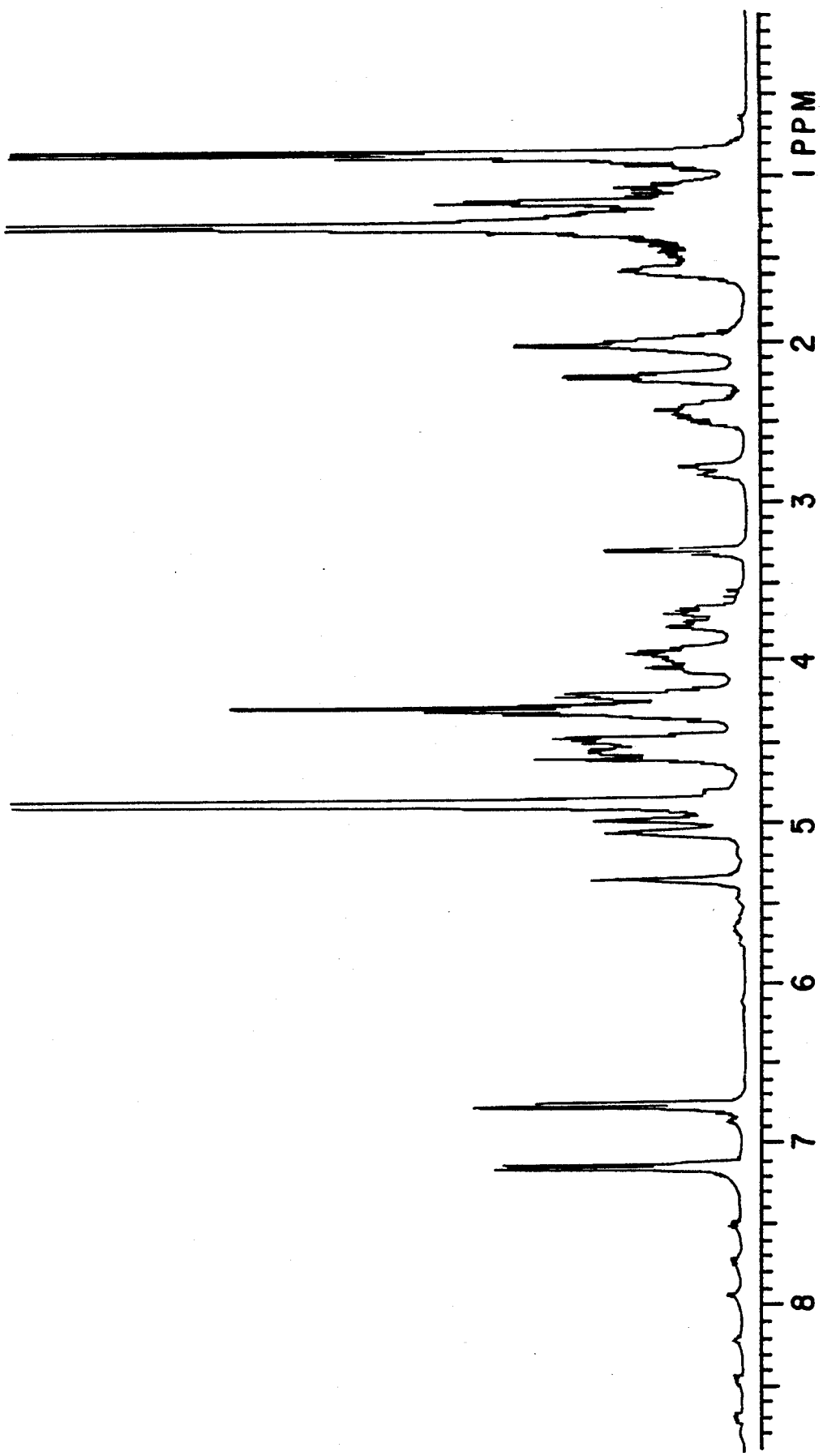

NMR SPECTRAL DATA $^1H$ NMR Spectrum in $CD_3OD$ at 400 MHz is seen in FIG. 2; and $^{13}C$ NMR Chemical Shifts ($CD_3OD$): 11.6, 19.7, 20.2, 20.8, 27.0, 28.0, 30.3, 30.6, 30.8, 31.2, 31.2, 32.9, 32.9, 34.8, 36.7, 38.1, 38.5, 39.4, 45.9, 51.2, 54.4, 55.3, 56.2, 57.0, 58.3, 62.5, 65.9, 68.2, 70.7, 70.8, 71.3, 71.9, 73.8, 75.8, 75.9, 77.0, 116.3(2C), 129.7(2C), 132.9, 158.4, 169.4, 172.5, 172.7, 173.2, 173.4, 174.5, 175.9, 177.2.

On the basis of these and other data, Compound I is believed with considerable certainty to have the structure indicated.

Compounds IA and IB are white solids, soluble in organic solvents such as methanol, ethanol, dimethylformamide, dimethyl sulfoxide, ethyl acetate an the like.

Compound I (IA and IB) has antifungal properties against both filamentous fungi and yeasts. It is particularly useful against organisms causing pathogenic mycotic infections such as *Candida albicans, Candida tropicalis, Candida pseudotropicalis, Candida parapsilosis* and the like.

Moreover, unlike a number of antifungal agents, such as amphotericin B, which while active against *Candida albicans* and other fungal pathogens are limited in their ability because of the untoward and dangerous side effects, the antifungal agent of the present invention is not only a very effective but is substantially free of undesirable side reactions.

Red blood cell lysis, a harmful and potentially fatal side reaction is shown by many compounds at concentrations approaching the therapeutic dose and this property has limited the applicability of these compounds as drugs. The compound of the present invention would require a concentration of drug far above that required for therapeutic use before red blood cell lysis could occur.

Compound I also may be employed against filamentous fungi such as Aspergillus species, Penicillium species, Fusarium species, Alternaria species, Neurospora species and the like.

Compound I also may be employed for the treatment of *Pneumocystis carinii*, the causative agent of a pneumonia which is of particular severity to immune compromised patients such as those with acquired immune deficiency syndrome (AIDS).

Compound I is conveniently produced by cultivating a mutagenized form of *Zalerion arboricola* produced as hereinafter described, and maintained in the Merck Culture Collection as MF5533. MF5533 was deposited under the Budapest Treaty in the Culture Collection of the American Type Culture Collection at 12301 Parklawn Drive, Rockville, Md. 20852 on Dec. 12, 1991, and was assigned accession number ATCC 74030.

*Zalerion arboricola* ATCC 74030 is a mutagenized form of *Zalerion arboricola* ATCC 20957 which in turn is a mutagenized form of ATCC 20868. This mutant may be produced by cultivating a frozen vegetative mycelia of *Z. arboricola* ATCC 20957 with a mutagen, followed by plating, incubating and isolating as hereinafter more fully described.

The major product in the cultivation of *Z. arboricola* MF5533 is Compound X represented by the formula

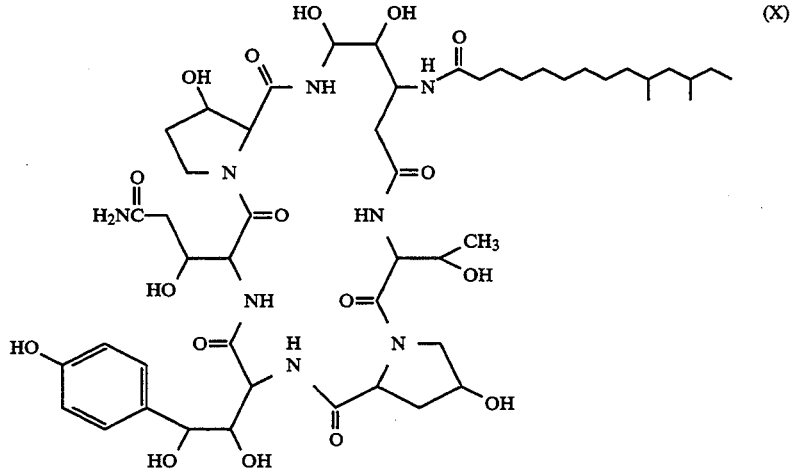

(X)

For the production of this mutant, a number of agents commonly used to produce mutants may be employed such as ultraviolet radiation, chemical mutagen, or inercalating agent. Suitable chemical mutagens include N-nitroso-N-methylurethane and N-methyl-N'-nitro-N-nitrosoguanidine.

In the present instance the *Z. arboricola* mutant MF5533, ATCC 74030 was obtained by inoculating a frozen vegetative mycelium of *Z. Arboricola* MF5404, ATCC 20957, disclosed and claimed in copending application Ser. No. 492,024, into a seed medium, adding N-methyl-N'-nitro-N-nitrosoguanidine and cultivating, thereafter plating a portion of the growth on potato dextrose agar and incubating to develop colonies, and then transferring the separate colonies to slants of potato dextrose agar and incubating for 14 days at 25° C. to obtain cultures of mutants of *Z. arboricola,* one of which was designated as 47-19, and subsequently maintained in the Merck Culture Collection as MF5533.

The colonial and morphological description of *Z. arboricola* MF5533 ATCC 74030 are as follows:

Colonies on potato-dextrose agar (Difco) at 20° C. are slow-growing, attaining a diameter of 8–12 mm in one week. Mature colonies (3–4 weeks) on potato-dextrose agar effuse, with submerged and aerial hyphae, surface halfly, lanose, or funiculose, dull to moderately shiny, forming raised, densely compact colonies, with a substromatic texture due to dense condidia formation. Colony color pale olive-brown, olive, olive-brown, finally olive-black, Isabella Color, Sayal Brown, Tawny-olive, Saccardo's Umber, Sepia, Brownish Olive, Raw Umber, Dark Olive, Olivaceous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1–3 um wide, thin- to slightly thick-walled, with walls smooth to slightly incrusted or verrucose. Aerial hyphae often adhering together in facicles. Setae and hyphopodia absent.

Conidiogeneous cells monoblastic, scattered to dense, integrated, terminal and intercalary, arising directly from undifferentiated hyphae, at right to slightly acute angles. Conidia originating as irregular chains filaments, or coils, later developing as compact, irregular masses of 6–25 cells. Individual condial cells, 3–6 um in diameter, globose, subglobose, or slightly irregular to lobed, smooth to finely verruculose, yellow-brown to olive brown.

Compound I may be obtained by cultivating *Z. arboricola* MF5533 in a suitable nutrient medium under conditions hereinafter described until a substantial amount of antifungal activity can be detected in the culture medium, harvesting by extracting the active components from the fermentation medium with a suitable solvent, concentrating the solution containing the desired component, then subjecting the concentrated material to chromatographic separation to isolate Compound I from other metabolites also present in the cultivation medium.

A suitable nutrient medium for producing Compound I is one containing sources of carbon and nitrogen assimilable by the microorganism and also containing low levels of inorganic salts. The medium may be supplemented with trace metals, although if complex sources of carbon and nitrogen are employed, the trace metals are usually present in the complex sources.

The sources of carbon include glycerol, sugars, sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, and complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Although the growth medium may be prepared in a conventional manner from the foregoing nutrients, the presence of certain nutrients and/or combination of nutrients favor the production of Compound I. Thus, ammonium salts are important as an immediate source of nitrogen and monobasic potassium phosphate is important for pH control. Mannitol is especially useful in compositions, not only for enhancing the amount of desired product formed but also in improving the rate of production of the desired product.

The cultivation medium may be either liquid or solid. Representatives suitable media for production of Compound I are the following:

| TG106 MEDIUM | |
|---|---|
| | per liter |
| D-Mannitol | 100 g |
| NZ-Amine type E* | 33 g |
| Fidco 8005 yeast extract | 10 g |
| $(NH_4)_2SO_4$ | 5 g |
| $KH_2PO_4$ | 9 g |
| P-2000 | 2 ml |

*Casein hydrolysate, Sheffield Products, Kraft, Inc.

| SP-5 MEDIUM | |
|---|---|
| | per liter |
| Mannitol | 80 g |
| $KH_2PO_4$ | 9 g |
| Cerelose | 10 g |
| PHARMAMEDIA* | 20 g | presterile pH 7.3
*yellow flour from embryo of cottonseed containing non-hydrolyzed globular protein Traders Protein, Buckeye Oilseed Products Co., Memphis Tenn.

| RG2 MEDIUM | | RG120 MEDIUM | |
|---|---|---|---|
| | per liter | | per liter |
| Mannitol | 44 g | Mannitol | 91 g |
| Corn Steep Liquor | 4 g | Corn Steep Liquor | 4 ml |
| Lard Water | 4 g | Lard Water | 4 g |
| Pectin | 10 g | Pectin | 10 g |
| $KH_2PO_4$ | 2 g | $KH_2PO_4$ | 2 g |
| Tomato Paste | 4 g | Tomato Paste | 4 g |
| Peptonized Milk | 4 g | Peptonized Milk | 4 g |
| Glycine | 2 g | Glycine | 2 g |
| Peanut Meal | 4 g | Peanut Meal | 4 g |
| pH adjusted to | 7.0 | pH adjusted to | 7.0 |

| TG102 MEDIUM | | TG103 MEDIUM | |
|---|---|---|---|
| | per liter | | per liter |
| D-Mannitol | 40 g | D-Mannitol | 40 g |
| Bacto-Peptone* | 33 g | Bacto-Peptone* | 33 g |
| Bacto-Yeast Extract | 10 g | Bacto-Yeast Extract | 10 g |
| $(NH_4)_2SO_4$ | 5 g | $(NH_4)_2SO_4$ | 5 g |
| $KH_2PO_4$ | 9 g | $KH_2PO_4$ | 9 g |
| no pH adjustment | | no pH adjustment | |

| S2 MEDIUM | | S6 MEDIUM | |
|---|---|---|---|
| | per liter | | per liter |
| D-Mannitol | 44 g | D-Mannitol | 44 g |
| $KH_2PO_4$ | 2 g | $KH_2PO_4$ | 2 g |
| Glycine | 2 g | Glycine | 2 g |
| Peptonized Milk | 15 g | Peptonized Milk | 15 g |
| Lactic acid | 2 g | Lactic acid | 2 g |
| Trace Elements | 10 ml | Trace Elements | 10 ml |
| | | Soybean oil | 10 g |
| pH 7.0 | | pH 7.0 | |
| (pre-sterilization) | | (pre-sterilization) | |

| F204 SOLID MEDIUM | | | |
|---|---|---|---|
| | per 250-ml flask | Base liquid | per liter |
| Millet | 15 g | ARDAMINE PH (**) | 33.0 g |
| Base liquid | 15 ml | Sodium Tartrate | 6.6 g |
| | | $FeSO_4.7H_2O$ | 0.66 g |
| | | Monosodium Glutamate | 6.6 ml |
| | | Corn oil | 6.6 ml |
| | | no pH adjustment | |

**Yeast autolysate, Yeast Products Inc. Clifton, New Jersey

| F4-SF SOLID MEDIUM | | | |
|---|---|---|---|
| | per 250-ml flask | Base liquid | per liter |
| Cracked corn | 15 g | Ardamine PH | 0.2 g |
| Base liquid | 10 ml | $H_2PO_4$ | 0.1 g |
| | | $MgSO_4.7H_2O$ | 0.1 g |
| | | Sodim Tartrate | 0.1 g |
| | | $FeSO_2.7H_2O$ | 0.01 g |
| | | $ZnSO_4.7H_2O$ | 0.01 g |
| | | no pH adjustment | |

Production of the desired compound using one of the foregoing or similar medium, is usually initiated by first inoculating a nutrient seed medium with a frozen vegetative mycelia of Z. arboricola MF 533, and the inoculated medium incubated for at least 3 days to produce a broth containing organisms which serves as seed in the production of the compounds of formula (I).

Instead of using all or an aliquot of the fermentation broth for production, an aliquot of the broth may be employed in a second stage productiion of seed medium. Depending on the size of the production contemplated, several stages of seed medium production may be carried out prior to utilization of the fermentation broth as seed in the ultimate production of Compound I. The seed medium is generally in the pH range of 5 to 8.1, optimally 6 to 7.5.

One useful seed medium is P34-2 medium of the following composition:

| | per liter |
|---|---|
| Corn steep liquor | 5 g |
| D-mannitol | 25 g |
| Glucose monohydrate | 10 g |
| Pharmamedia | 20 g |
| $KH_2PO_4$ | 9 g |
| $FeSO_4.7H_2O$ | 10 mg |
| $MnSO_4.4H_2O$ | 10 mg |
| $CuCl_2.2H_2O$ | 0.25 mg |
| $CaCl_2.2H_2O$ | 1 mg |

|  | per liter |
|---|---|
| $H_3BO_3$ | 0.56 mg |
| $(NH_4)_6Mo_7O_{24}.H_2O$ | 0.19 mg |
| $ZnSO_4.7H_2O$ | 2 mg | per/liter

Another useful seed medium is KF medium of the following composition:

|  | per/liter |
|---|---|
| Corn steep liquor | 5 g |
| Tomato paste | 40 g |
| Oat flour | 10 g |
| Glucose | 10 g |
| $FeSO_4.7H_2O$ | 10 mg |
| $MnSO_4.4H_2O$ | 10 mg |
| $CuCl_2.2H_2O$ | 0.25 mg |
| $CaCl_2.2H_2O$ | 1 mg |
| $H_3BO_3$ | 0.56 mg |
| $(NH_4)_6Mo_7O_{24}.H_2O$ | 0.19 mg |
| $ZnSO_4.7H_2O$ | 2 mg |

In carrying out the process, a slant section of a preserved culture of MF5533 ATCC 20958 is inoculated into an appropriate seed medium and the flasks incubated with or without agitation at temperatures in the range of from about 15° C. to about 30° C. for from 2 to 30 days, preferably 20° to 28° C. for 2 to 14 days. Agitation when employed is preferably in the range of from 150 to 220 rpm but may be up to 400 rpm. When growth is abundant, usually between 2 and 5 days, the growth may be used to inoculate the production medium for the production of the compounds of this invention. Preferably however, a second stage fermentation and, frequently a third or fourth stage fermentation are carried out by inoculating with a portion of the culture growth and then employing similar conditions and incubation time of from about 1 to 6 days. The growth then is employed to inoculate the production medium.

The fermentation production medium inoculated with the culture growth is incubated for 3 to 30 days, usually 7 to 14 days, with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°–28° C. are most preferred. The pH of the nutrient medium suitable for producing the instant compounds can vary from about 5.0 to 8.5 with a preferred range of from about 5.5 to 6.0. After the appropriate period-for the production of the desired compound or compounds, the latter is recovered from the fermentation medium as hereinafter more fully described.

HARVEST AND ISOLATION

After completion of the cultivation, Compound I is harvested and isolated from the medium. The exact steps may vary somewhat on whether the fermentation is carried out in liquid or solid medium.

When the fermentation is carried out on a solid medium, the first step may be adding an alcoholic solvent to the fermentation medium, thoroughly mixing, then filtering, recovering and concentrating the aqueous alcohol filtrate. The concentrated filtrate may be first back-extracted or washed with a lower aliphatic hydrocarbon solvent such as hexane or other alkane to remove alkane soluble impurities.

When the fermentation is carried out in a liquid medium, in one method, the mycelial solids may be separated by filtration or centrifugation and recovered from the fermentation medium. Alcohol is added to the mycelial cake, and the mycelial solid thoroughly mixed with a lower alkanol to extract the desired product and the mixture filtered or centrifuged, and the filtrate or supernatant collected and concentrated. In an alternative method, the whole broth can be extracted by the addition of one volume of lower alkanol, preferably methanol, and filtered or centrifuged to remove solid impurities.

The lower alkanol suitable for extracting the active agent from the solid nutrient medium or the mycelial pad obtained on centrifugation or filtration include methanol, ethanol, isopropanol or higher alkanols. Methanol is preferred. The alkanol extract from either separation is then placed onto a column for chromatographic separation steps. Adsorbents available commercially such as styrenedivinylbenzene copolymers available commercially as "DIAION"HP-20, HP-30, HP-40, SP-207 (Mitsubishi Chemical Industries, Ltd.) and "AMBERLITE" XAD-2, XAD-4, XAD-16 (Rohm and Haas Co.), may be employed for the intial isolations.

In carrying out the separation steps, the composition of the alkanol extract is adjusted to 50 percent water and adsorbed on the HP-20 or other selected resin and then eluted with 100 percent alkanol, preferably methanol.

Conventional column chromatography may be employed. When conventional chromatographic separation is employed, "SEPHADEX" LH-20 (Pharmacia) or silica gel may be employed although silica gel is preferred.

In the fractionation and recovery of the active component by chromatography on silica gel, ester/alcohol/water or dichloromethane/alcohol/water may be employed to provide good separations. A mixture of ethyl acetate, methanol, and water or 5 percent aqueous acetic acid has been found to be especially useful. When a dextran adsorbent such as "SEPHADEX" LH-20, is employed, a chlorohydrocarbon/hydrocarbon/alcohol solvent system may be employed. A mixture of methylene chloride/hexane/methanol has been found to be expecially useful.

In carrying out the HPLC separation, the alcohol solution containing material recovered from the conventional chromatography is concentrated and the residue dissolved in methylene chloride/methanol/"water or ethyl acetate/methanol/water in the same ratio as found in the mobile phase and placed on a column packed with commercial silica gel resin and eluted at about 800–2000 psi which produces a flow rate of about 10 ml/min. The separation is monitored by UV at 276 nm.

Compound I is active against many fungi, and also against *Pneumocystis carinii.*

The antifungal properties may be illustrated with the minimum fungicidal concentration (MFC) determinations against certain Candida organisms in a microbroth dilution assay carried out in Yeast Nitrogen Base (Difco) with 1 percent dextrose (YNBD). In carrying out the assay, Compound I was solubilized in 10 percent dimethyl sulfoxide (DMSO) and diluted to 2560 μg/ml. The compound was then diluted to 256 μg/ml in YNBD. 0.15 ml of the suspension was dispensed to the top row of a 96-well plate (each well containing 0.15 ml of YNDB) resulting in a drug concentration of 128 µg/ml. Two-fold dilutions were then made from the top row to obtain final drug concentrations ranging from 128 to 0.06 µg/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of 1–5×10⁶ colony forming units (CFU)/ml.

96-well microplates were inoculated using a MIC-2000 (Dynatech) which delivers 1.5 µl per well yielding a final inoculum per well of 1.5–7.5×10³ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 µl samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot. The results (three samples) are seen in the following table:

| Fungi Strain No. | Minimum Fungicidal Concentration (µg/ml) | |
|---|---|---|
| | Compound IA | Compound IB |
| *Candida albicans* | | |
| MY 1055 | 2 | 1 |
| MY 1028 | 2 | 0.5 |
| MY 1750 | 4 | 1 |
| *Candida tropicalis* | | |
| MY 1012 | 1 | 0.12 |
| *Candida pseudotropicalis* | | |
| MY 1100 | 4 | 2 |

Compound I is useful for inhibiting or alleviating *Pneumocystis carinii* infections. In a representative study, the effectiveness of Compound I in rats were determined. Sprague-Dawley rats (weighing approximatley 250 g) were immunosuppressed with dexasone in the drinking water (2 mg/ml) and maintained on a low protein diet for 5 weeks to induce the development of *Pneumocystis* pneumonia from a latent infection. Before drug treatment 2 rats were sacrificed to confirm the presence of *Pneumocystis carinii* pneumonia (PCP); both rats had infections. The remaining rats (weighing approximately 150 g) were distributed into groups of 6 and injected twice daily for four days subcutaneously with compound in 0.25 ml of vehicle (10% DMSO in water or water). The control group of 5 rats received vehicle alone. All animals continued to receive dexasone in the drinking water and low protein diet during the drug treatment period. At the completion of treatment all animals were sacrificed, the lungs were removed and processed, and the extent of disease determined by microscopic analysis of stained slides. The results of this study are shown as the log mean number of cysts per animal lung as determined by examining 20-1000X microscopic fields (as seen in the following table) and the standard of error of the geometric mean. All groups were compared using the student t-test and results marked (*) are significant.

TABLE

| | Log Mean # Cysts (± SEGM) | Reduction of Cysts | Survivors |
|---|---|---|---|
| DMSO Control | 7.26 ± 12 | — | 6/6 |
| Compound IA | | | |
| 1.20 mg/kg | 5.58 ± .11* | 97.9% | 5/6 |
| 0.60 mg/kg | 5.68 ± .19* | 97.4% | 6/6 |
| 0.30 mg/kg | 5.99 ± .18* | 94.6% | 5/6 |
| 0.15 mg/kg | 6.32 ± .17* | 88.5% | 6/6 |
| Compound IB | | | |
| 0.60 mg/kg | 5.41 ± .17* | 99.1% | 6/6 |
| 0.30 mg/kg | 5.22 ± .10* | 99.4% | 6/6 |
| 0.15 mg/kg | 5.59 ± .11* | 98.7% | 6/6 |
| 0.07 mg/kg | 5.97 ± .18* | 96.8% | 6/6 |
| 0.03 mg/kg | 6.16 ± .14* | 95.0% | 6/6 |

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent of weight of Compound I. Concentrate compositions suitable for dilutions prior to use may contain 90 percent or more by weight. The compositions include compositions suitable for oral, rectal, topical, parenteral (including subcutaneous, intramuscular, and intravenous), pulmonary (nasal or buccal inhalation), nasal administration, or insufflation. The compositions may be prepacked by intimately mixing Compound I with the components suitable for the medium desired.

When the compound is for antifungal use any method of administration may be used. For treating mycotic infection oral administration is frequently preferred. When oral administration is to be employed, it may be with a liquid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound I also may be formulated in therapeutic compositions for intravenous or intraperitoneal injection and may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/propylene glycol or polyethyleglycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The compounds may also be delivered as powders which may be formulated and the powder composition may be inhaled with the aid of an insufflation powder inhaler device. The preferred delivery system for inhalation is a metered dose inhalation (MI)I) aerosol, which may be formulated as a suspension or solution of Compound I in suitable propellants, such as fluorocarbons or hydrocarbons.

Another method of administration is insufflation, particularly if the infection has spread to the ears and other body cavities.

If the application is to be topical, the drug may be formulated in conventional creams and ointments such as white petrolatum, anhydrous lanolin, cetyl alcohol, cold cream, glyceryl monostearate, rose water and the like. Usually a 1 to 2 percent cream solution is prepared and applied to the area to be treated.

The following examples illustrate the invention but are not to be construed as limiting.

EXAMPLE 1

Preparation of Mutant *Z. arboricola* MF 5533 ATTCC 74030

A frozen vegetative mycelium of *Z. arboricola* MF5404 ATCC 20957 was inoculated into 50 milliliters of KF seed medium contained in a 250 milliliter Erlenmeyer flask and N-methyl-N'-nitro-N-nitrosoguanidine (NTG) was added to a final concentration of 7.5 micrograms per milliliter. The flask was shaken at 220 rpm at 25° C. for five days to obtain broth containing cells grown in the presence of NTG. A portion of the broth was plated on the surface of potato dextrose agar and the plates incubated for 14 days at 25° C. to obtain spores of the microorganism. The spores were harvested, diluted in sterile saline and plated on the surface of potato dextrose agar and incubated at 25° C. for 7 days for colony formation. The colonies were isolated by transferring each colony to separate slants of potato dextrose agar. The inoculated slants were incubated at 25° C. for 14 days and a plug from the slants separately taken and inoculated into 20 milliliters of KF medium to produce seeds, then, 2 milliliters of the seed used to inoculate 40 milliliters of SP-5 medium which was then incubated at 25° C. for 14 days. The broth then was extracted with methanol and the extract tested for the production of Compound X and other components by HPLC. One of the slants designated Culture 47-19 was used in the production hereinafter described. Culture 47-19 was subsequently re-isolated and preserved in the Merck Culture Collection as MF 5533.

EXAMPLE 2

Production of Compound I Fermentation

Seed cultures were first prepared in several stages. As an initial step, 54 milliliters of P34-2 medium was inoculated with a plug from a frozen vial of *Zalerion arboricola* tentatively designated Culture 7-19 and subsequently re-isolated and preserved in the Merck Culture Collection as MF5533. The inoculated medium was incubated with shaking at 220 rpm at 25° C. for four days. A twenty-milliliter sample of this seed medium was used to inoculate each of four 2-liter flasks containing 500 milliliters of P34-2 medium and the inoculated medium incubated at 25° C. for four days at 220 rpm. The flask contents were then pooled and used to inoculate a 300-liter seed fermenter containing 180 liters of P34-2 medium and 2 milliliters/liter of polypropylene glycol P-2000 to reduce foaming. The fermenter was operated for six days at a temperature of 25° C, an air flow of 90 liters per minutes, a pressure of 0.7 kg/cm$^2$ gauge, and an agitator speed of 200 rpm. A 25 liter sample of this seed then was used to inoculate an 800 liter seed fermenter containing 475 liters of P34-2 medium and 2 milliliter/liter of P-2000 and cultivated for four days at 25° C., air flow of 250 liter/minute, a pressure of 0.7 kg/cm$^2$ gauge and agitator speed of 150 rpm.

425 liters of the seed broth thus prepared was inoculated into 13,700 liters of TG 106 medium in a 19,000 liter production fermenter. Fermentation of the mixture was carried out at a temperature of 25° C., air flow of 6300 liters/minute, a pressure of 0.7 kg/cm$^2$ gauge and agitator speed of 80 rpm. The pH was allowed to decrease from an initial value of 6.0 to 5.5 and then maintained at 5.5±0.2 using sodium hydroxide or sulfuric acid. The cultivation was continued for twelve days, after which time the broth was harvested for product isolation.

EXAMPLE 3

Isolation of Compound IA

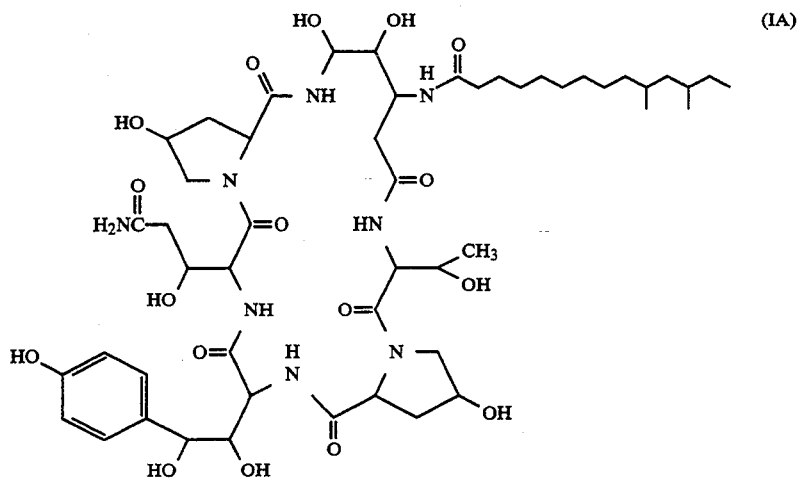

(IA)

3100 gallons of whole broth was first extracted with 1900 gallons of methanol. The methanol was clarified by centrifugation to obtain 4250 gallons of clarified liquid as first extract and 650 gallons of solid. The latter was re-extracted with 1500 gallons of methanol and centrifuged to obtain 1550 gallons of clarified liquid as second extract. The solids from this centrifugation were extracted with 1500 gallons of 80 percent aqueous methanol and centrifuged to obtain a third extract.

The first extract was loaded on an SP-207 (brominated polystyrene-divinylbenzene copolymer) adsorption column and washed with 65% aqueous methanol. Some product breakthrough was noted in the 65 percent methanol wash.

The 65 percent methanol wash and selected side outs from the first SP-207 column, amounting to 900 gallons, were combined with the second and third extracts from the whole broth and combined extracts totalling 4050 gallons were absorbed on an SP-207 column and eluted with 100 percent methanol.

The rich cut eluate from the first SP-207 column was diluted, adsorbed and eluted with 100 percent methanol from an HP-20 columns. The rich cut eluate from the second SP-207 column was combined, diluted with water, adsorbed to two HP-20 columns, and eluted with 100 percent methanol.

The three HP-20 rich cut eluates were combined, diluted With water and then adsorbed and eluted with 100 percent methanol from an SP-207 column for concentration and dewatering. the rich cut was concentrated 4× by distillation.

To a 500 ml aliqnot of the 4× concentrate from the foregoing columns was added 4.5 liters of isopropyl acetate to separate the product which precipitates from P-2000 which remains in solution.

The precipitate was then prepared for preparative HPLC to be carried out on a commercial column identified as Doff-Oliver Peak Performer equipped with a Prochrom LC 150 VE 15 cm. column charged with 3 kilograms of 'MATREX' irregular silica gel (AMICON) of 20 µm particle size, 60 Å pore size. In the preparation the precipitate was first filtered, vacuum dried, and dissolved in 550 milliliters of 2:2:1 ethyl acetate/methanol/5% acetic acid solvent mixture. The solvent composition was then adjusted to the feed composition of 76/16/8 ethyl acetate/methanol/5% aqueous acetic acid and 715 milliliters of the mixture was immediately injected onto the Prochram LC 150 VE column at a flow rate of 605 ml/min. using the mobile phase of 80/10/5 ethyl acetate/methanol/5% aqueous acetic acid and twenty-two 2-liter fractions collected.

Fraction 16 was concentrated to dryness and 100 milligrams of it was reconstituted in 2 milliliters of 80:20:2 methylene chloride/methanol/water. The solution was filtered to clarify it and the clear solution injected onto a 50 centimeter×22.5 millimeter WHATMAN silica gel HPLC column. The mobile phase for the chromatography was 80:20:2 methylene chloride/methanol/water and the flow rate was 10 milliliters/minute. The chromatography was monitored using UV detector at 276 nm and also by analytical HPLC of the fractions. Both detection methods indicated a baseline separation of Compound IA, IB and X, all of which were present in the original mixture.

A total of nine identical injections were performed in the manner above indicated and the factions containing compound IA were combined, concentrated to dryness and reconstituted into 100 milliliters of 50:50 methanol/water. This solution was adsorbed to 20 milliliters of HP-20, eluted with methanol and dried under vacuum to obtain 91 milligrams of Compound IA.

EXAMPLE 4

Isolation of Compound IB

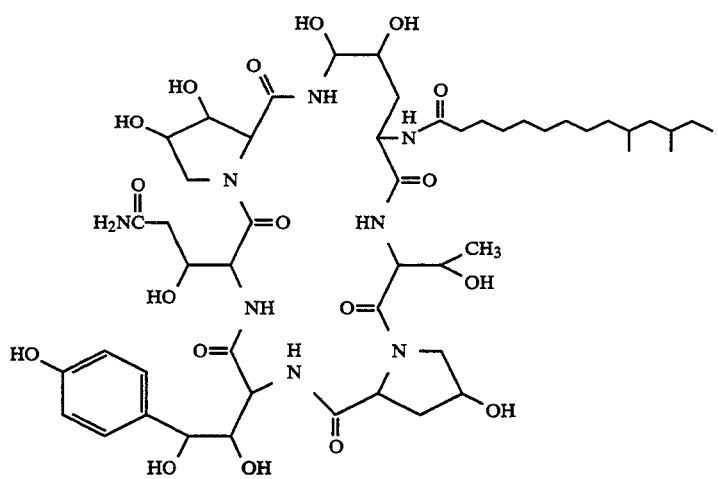

The remaining 4× concentrate from the third SP-207 column in Example 3 was added to 10 volumes of isopropyl acetate to precipitate Compound X, IA and IB. The precipitate was collected by centrifugation and the material chromatographed on four 500 ml silica gel columns eluted with 85:10:5 ethyl acetate/methanol/5% aqueous acetic acid. A composite sample from one of the silica columns containing 60 g of Compound IB and 20 g of Compound IA (as determined by HPLC) was chromatographed on a 150 liter silica column run in a similar manner. Four 50 gallon fractions were collected followed by twenty-three 15 gallon fractions. One of the 15 gallon fractions rich in Compound IB (>95% as determined by HPLC) was concentrated to dryness, reconstituted in ethyl acetate/methanol/water (76/16/8) and further purified on a 1 liter silica column, eluted with 85/10/5 ethyl acetate/methanol/5% aqueous acetic acid. The rich cuts were combined, concentrated, redissolved in 50/50 MeOH/$H_2O$ and desilicated on a 40 ml HP-20 column. Compound IB was eluted with 100% MeOH. The cuts rich in Compound IB were combined, subjected to a rotary evaporator to vaporize the methanol and obtain an aqueous solution which was lyophilized to obtain Compound IB as a white powder. The white powder had the spectral characteristics set forth previously for Compound IB.

EXAMPLE 5

In a manner similar to that described in Part A of Example 1, mutant MF 5533 was obtained from MF 5404 except that the seed from the seed flasks were used to inoculate 40 milliliters of TG-106 medium and the latter incubated at 25° C. with shaking at 25° C. for 14 days.

EXAMPLE 6

1000 tablets, each containing 500 milligrams of Compound IA are prepared from the following formulation:

| Compound | Grams |
|---|---|
| Compound IA | 500 |
| Starch | 750 |
| Dibasic calcium phoshate hydrous | 5000 |
| Calcium stearate | 2.5 |

The finely powered ingredients are mixed well and granulated with 10 percent starch paste. The granulation is dried and compressed into tablets.

EXAMPLE 7

1000 hard gelatin capsules, each containing 500 milligrams of Compound IB are prepared from the following formulation:

| Compound | Grams |
|---|---|
| Compound IB | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 8

250 milliliters of an injectable suspension are prepared by conventional procedures having the following formulation:

| 5% DMSO/water | 250 milliliters |
|---|---|
| Compound IB | 400 milligrams |

The ingredients are blended and thereafter sterilized for use.

EXAMPLE 9

An ointment suitable for topical application may be prepared by intimately dispersing 13 milligrams of Compound IA in 1 gram of commercially available polyethylene/hydrocarbon gel.

EXAMPLE 10

An aerosol composition may be prepared having the following formulation:

|  | Per Canister |
| --- | --- |
| Compound IB | 24 mg |
| Lecithin NF, liquid concentrate | 1.2 mg |
| Trichlorofluoromethane | 4.025 g |
| Dichlorodefluoromethane | 12.15 g |

PREPARATION OF MF5404

A culture of *Z. arboricola* ATCC 20868 was grown on potato dextrose agar in petri plates at 25° C. for 3 weeks. Ten milliliters of 0.3M TRIS buffer, pH 7, were added to the plates and the spores scraped off the surface into the buffer with a sterile cotton swab. The suspension in the buffer was decanted off and the procedure repeated twice. The spore suspensions were combined and filtered through glass wool to remove large clusters of spores. The suspension filtrate was centrifuged at first at 600 rpm then at 700 rpm and finally at 800 rpm, each time for 3 minutes with the pellet being discarded after each centrifugation. The supernatant liquid from the third centrifugation was then centrifuged at 3000 rpm for 5 minutes. The pellet from this centrifugation was resuspended in 3 milliliters of 0.3M TRIS buffer and used for mutagenic treatment. This suspension contained from $10^3$ to $10^4$ spores per milliliter.

To the spore suspension was added 100 µg/ml of N-nitroso-N-methylurethane and the resulting mixture shaken at 300 rpm for 20 minutes at room temperature. At the end of this period, the mixture was centrifuged and the supernatant liquid was removed. The pellet was washed twice with 0.3M TRIS buffer pH 7.0 and then resuspended in the same buffer and after appropriate dilutions plated on potato dextrose agar for forming isolated colonies. The plates were incubated at 25° C. for two weeks for colony formation. The colonies were isolated by separately transferring to slants of potato dextrose agar. The inoculated slants were incubated at 25° C. for 10–14 days and a plug from the slants taken and tested for the production of Compounds X and other components in the fermentation by HPLC assay. A plug from one of the slants initially designated as Z7-9, was placed in the Merck Culture Collection as MF 5404 and deposited with the American Type Culture Collection as ATCC 20957.

What is claimed is:

1. A method for producing a compound having the formula

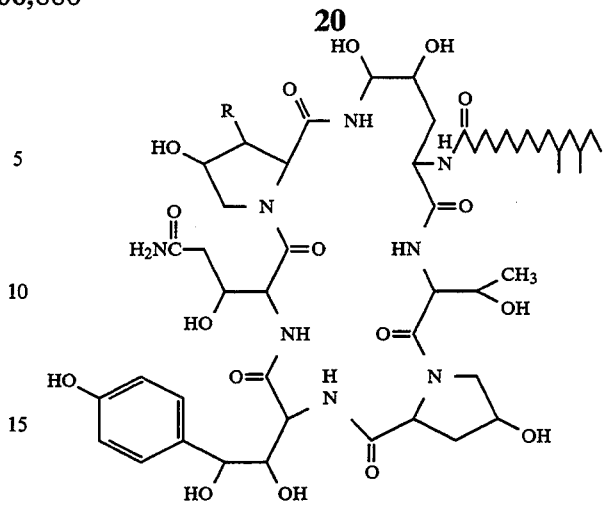
wherein R is hydrogen or hydroxyl comprising cultivating Zalerion arboricola MF 5533, ATCC 74030, in a nutrient medium containing assimilable sources of carbon, nitrogen and inorganic salts under aerobic conditions and thereafter separating the compound from the medium.
* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( x i ) SEQUENCE DESCRIPTION: SEQ ID NO:1:

```
Xaa  Thr  Xaa  Xaa  Xaa  Xaa
 1                 5
```

( 2 ) INFORMATION FOR SEQ ID NO:2:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( x i ) SEQUENCE DESCRIPTION: SEQ ID NO:2:

```
Xaa  Thr  Xaa  Xaa  Xaa  Xaa
 1                 5
```

( 2 ) INFORMATION FOR SEQ ID NO:3:

( i ) SEQUENCE CHARACTERISTICS:
( A ) LENGTH: 6
( B ) TYPE: AMINO ACID
( C ) STRANDEDNESS: Not Relevant
( D ) TOPOLOGY: CIRCULAR ( x i ) SEQUENCE DESCRIPTION: SEQ ID NO:3:

```
Xaa  Thr  Xaa  Xaa  Xaa  Xaa
 1                 5
```